United States Patent [19]

Warden

[11] Patent Number: 5,143,333
[45] Date of Patent: Sep. 1, 1992

[54] WEIGHT COUNTERBALANCE MEANS

[75] Inventor: Hans-Erik Warden, Upplands, Sweden

[73] Assignee: Siemens Aktiengesellschaft, Munich, Fed. Rep. of Germany

[21] Appl. No.: 570,901

[22] Filed: Aug. 22, 1990

[30] Foreign Application Priority Data

Aug. 25, 1989 [SE] Sweden ............................ 89028310

[51] Int. Cl.⁵ .............................................. F16L 3/00
[52] U.S. Cl. ................................ 248/123.1; 248/281.1
[58] Field of Search .............. 248/123.1, 292.1, 280.1, 248/281.1, 364; 108/2

[56] References Cited

U.S. PATENT DOCUMENTS

| | | | |
|---|---|---|---|
| 1,347,846 | 7/1920 | Gelb | 248/123.1 X |
| 2,548,476 | 4/1951 | Horstmann | 248/281.1 |
| 4,101,779 | 7/1978 | Schmedemann | |
| 4,318,538 | 3/1982 | Janssen | |
| 4,335,315 | 6/1982 | Waerve et al. | 248/281.1 X |
| 4,344,595 | 8/1982 | Heller et al. | 248/123.1 X |
| 4,709,588 | 12/1987 | Cordes et al. | 248/281.1 X |

FOREIGN PATENT DOCUMENTS

| | | |
|---|---|---|
| 939348 | 2/1956 | Fed. Rep. of Germany |
| 2704555 | 8/1978 | Fed. Rep. of Germany |
| 3312137 | 10/1984 | Fed. Rep. of Germany |
| 217261 | 2/1942 | Switzerland ............................ 108/2 |

Primary Examiner—Carl D. Friedman
Assistant Examiner—Korie H. Chan
Attorney, Agent, or Firm—Hill, Van Santen, Steadman & Simpson

[57] ABSTRACT

Weight counterbalancing means for an articulating arm comprising first and second articulating arm members. One end of the first arm member is pivotally secured to a base and operative to pivot around a first horizontal axis. The second arm member is pivotally secured to the other end of the first arm member and is operative to pivot about a second horizontal axis. Each arm member is provided with a lever member that is part of a parallelogram system whose connecting nodes in part comprise the free end of the lever member of the first arm member, the pivot axis of the second arm member, and the free end of the lever member of the second arm member, a remaining connecting node in the parallelogram system being subject to a force that serves as a counterbalance for the articulating arm around the first horizontal axis, so that the articulating arm is held in equilibrium in every position.

12 Claims, 2 Drawing Sheets

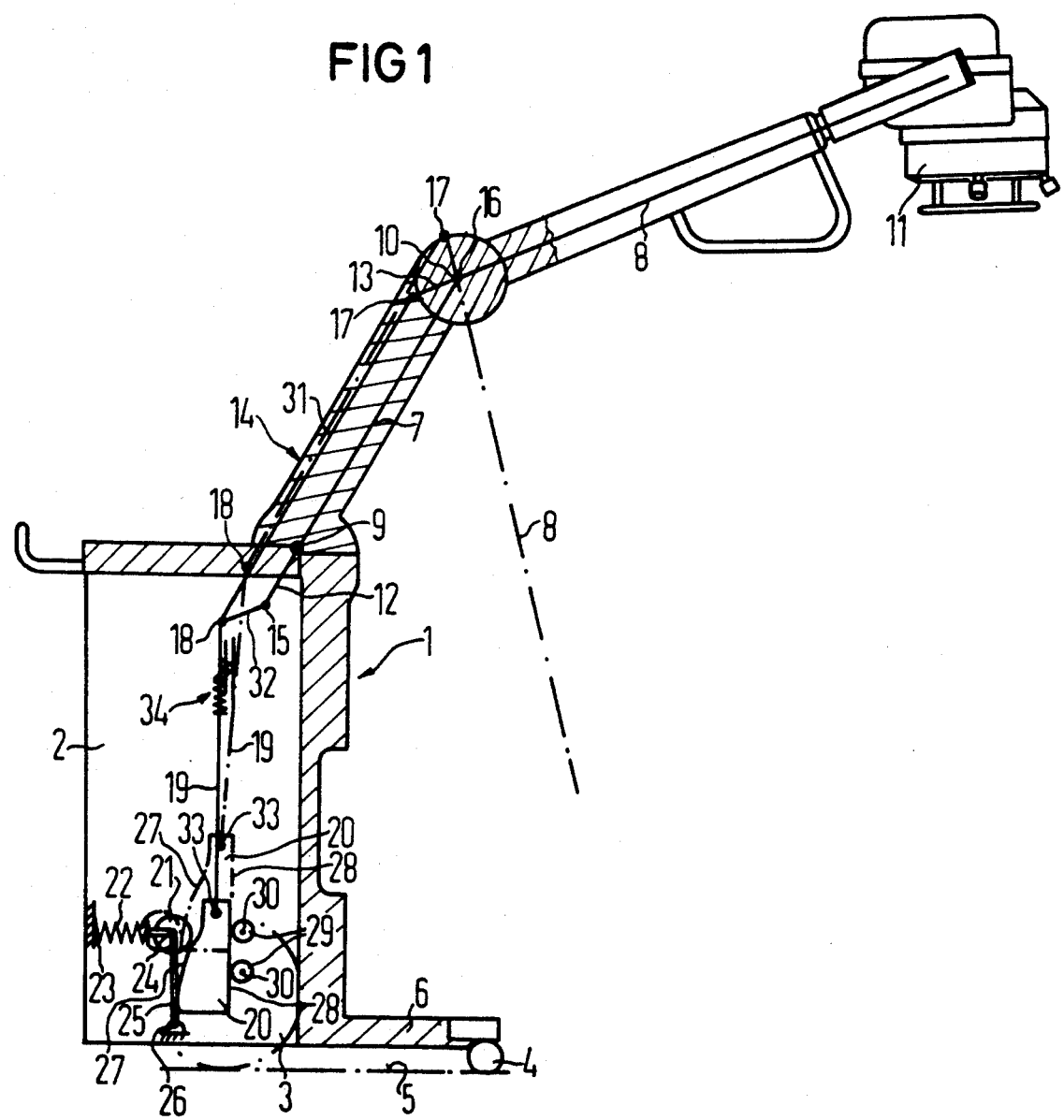

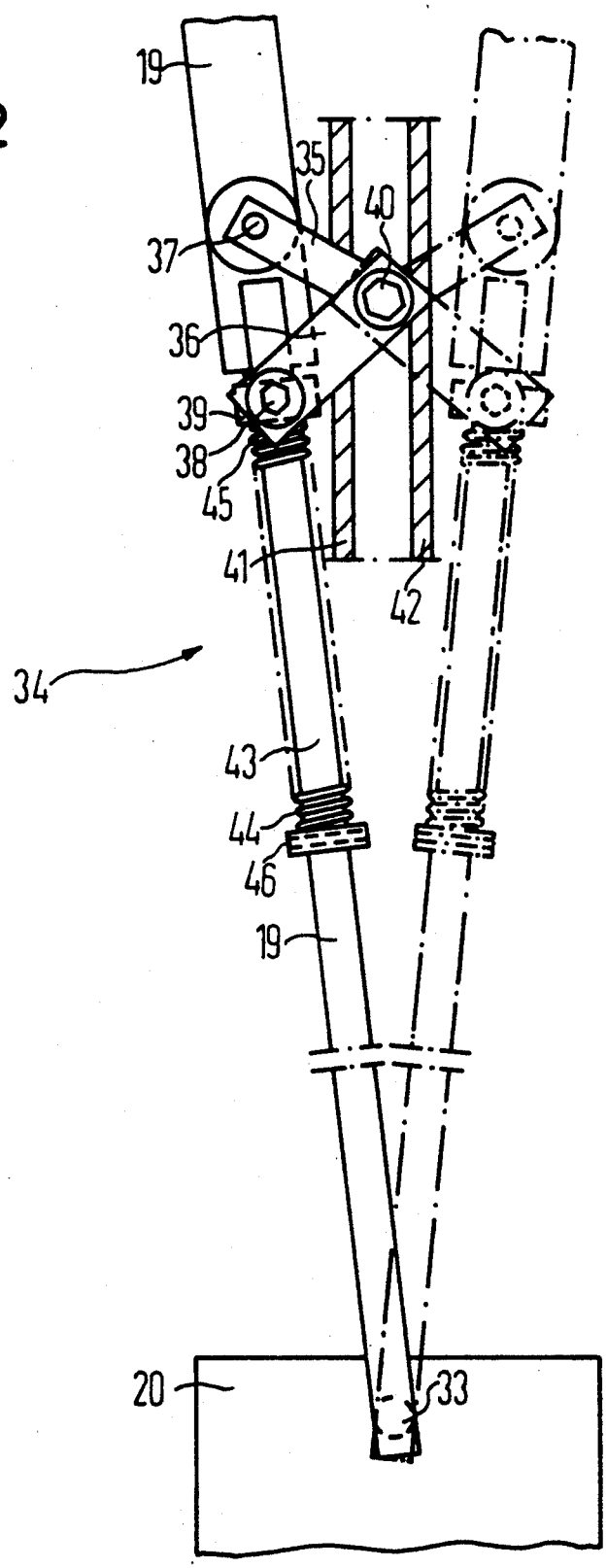

5,143,333

WEIGHT COUNTERBALANCE MEANS

BACKGROUND OF THE INVENTION

The invention generally relates to a weight counterbalance means. More specifically, the invention relates to a weight counterbalance means for a two-jointed support arm. Yet more specifically, the invention relates to a weight counterbalance means for a bipartite bracket mechanism in an x-ray apparatus having first and second brackets (arm members), wherein one end of the first bracket is rotatably seated around a horizontal, first shaft at the base of the x-ray apparatus and the other end is rotatably connected via a second shaft to one end of the second bracket, the other end of which is secured to an x-ray tube.

A weight counterbalance means of the type to which the invention relates is disclosed by German published application 27 04 555, the teachings of which are incorporated herein by reference. In the disclosed apparatus, every bracket (arm member) is balanced out by an associated roller that is pressed by a spring against a cam plate associated with the bracket. In relationship to the rotational center of its respective cam plate, the force of each roller is directed such that a torque arises at the cam plate that serves to hold the torque acting on the bracket in equilibrium in every bracket position. Gear wheels and chains are employed as means for transmitting the motion between the cam plates and the respective shafts of the brackets.

SUMMARY OF THE INVENTION

The present invention creates a weight counterbalancing means that is light weight, simple in structural format, and as a result thereof, is relatively inexpensive to construct.

To these ends, in an embodiment, the invention provides a parallelogram weight counterbalancing construction for a jointed or articulating arm having at least first and second arm members hingedly secured together and wherein the end of the first arm is also hingedly secured to a base. The parallelogram construction preferably is provided via lever members secured at the hinged ends of the first and second arm members, three nodes of the parallelogram comprising the free ends of the lever arms secured to the arm members and the hinge connecting the first and second arm members. The fourth node of the parallelogram preferably is positioned at the end of a stay hingedly connected to a free end of the lever member secured to the base end of the first arm member. Then, the fourth node preferably is subject to a force that completely counterbalances the weight of the entire jointed arm.

In one embodiment of the invention, the respective lengths of the lever arms preferably are selected such that the force that counterbalances the jointed arm is constant independently of the position of the jointed arm.

In another embodiment of the invention, a wedge-shaped member whose movement is restricted to a vertical direction is suspended from the fourth node and a spring is provided that acts against a sloped surface of the weight such that a sub-force corresponding to the constant force arises. As a result thereof, only one spring is required to influence the wedge-shaped member in order to counterbalance the torques acting on the arm members of the jointed arm in every position. As a result of this design, an advantage derives in that the arm member that is secured to the one end of the arm member secured to the base can be displaced in a horizontal plane without the wedge-shaped member moving in the vertical direction to a noteworthy degree. In such a motion sequence, the spring is not moved, this meaning lower frictional losses and lower wear or, respectively, fatigue of the spring.

In one embodiment of the invention, the wedge-shaped member is connected to the fourth connecting node via a brace.

In one embodiment of the invention, the wedge-shaped member is connected to a brace which in turn is hingedly connected to the stray, so that an articulated axis between the first and second arm members is seated in a part rigidly connected to the base such that the articulated axis is displaceable mainly only in a vertical plane, the end of the second arm member connected to the x-ray apparatus being influenced by a force in the axial direction of the brace against the end of the first arm member connected to the second arm member. A force-compensating arrangement is thereby obtained that compensates for the lateral forces to which the brace is subjected during specific adjustments of the bracket.

These and other features and aspects of the invention set forth in greater detail in the following detailed description of the presently preferred embodiments and accompanying drawings.

BRIEF DESCRIPTION OF THE DRAWINGS

FIG. 1 is a side view of a mobile x-ray apparatus having a weigh counterbalancing means embodying principles of the invention.

FIG. 2 illustrates a force-compensating arrangement for the weight counterbalancing means of FIG. 1.

DETAILED DESCRIPTION OF THE PRESENTLY PREFERRED EMBODIMENTS

In FIG. 1 there is illustrated a mobile x-ray apparatus 1 having a truck 2 that is provided with two running wheels 3 and two steering wheels 4 and that is movable on a floor 5. The steering wheels 4 are secured to an extension 6 that extends from the truck 2.

The x-ray apparatus 1 is provided with a bipartite bracket mechanism or articulated arm 1 having a first bracket or arm member 7 and a second bracket or arm member 8. As illustrated, one end of the first arm member 7 (the base end) is attached to the truck 2 so as to be rotatable around a horizontal, first shaft 9 that is secured to the upper side of the truck 2. The truck 2 thus serves as a base member.

The other end (the free end i.e., that end not attached to the truck 2) of the first arm member 7 is pivotally connected to one end (the base end) of the second arm member 8 via a shaft 10 so that the second arm member 8 is operative to pivot relative to the arm member 7. An x-ray tube 11 is secured at the other end (the free end i.e., the end not attached to the first art member 7) of the arm member 8.

The arm members 7 and 8 are each provided with a lever arm or lever member 12 and 13, respectively, the lever arms 12 and 13 comprising a part of a parallelogram system 14 having connecting nodes 15, 16, 17, and 18. The connecting nodes 15, 16, and 17 are positioned at the free end of the lever arm 12 of the first arm member 7, at the second shaft 10, and at the free end of the lever arm 13 of the second arm member 8, respectively.

The remaining connecting node 18 in the parallelogram system is provided at the connection of a longitudinal stay 31 and a cross stay 32 whose other ends are connected to the free ends of the lever members 13 and 12, respectively. As illustrated, the node 18 is also connected via a brace 19 to a wedge-shaped cam plate 20. Preferably, the connecting node 18 is supported away from the free end of the lever arm 12 by the cross stay 32, which comprises one side of the parallelogram.

As a result of the force of a spring 22 that is clamped between a fastening point 23 at the truck 2 and a shaft 24 of a roller 21, the roller 21 presses against a surface 27 of the cam plate 20. The shaft 24 of the roller 21 is also connected in an articulated fashion to a further fastening point 26 at the truck 2 via a rod 25 that is attached essentially vertically relative to the longitudinal direction of the spring 22. In this way, the roller 21 mainly presses in a horizontal direction against the surface 27 of the cam plate 20 under the bias of the spring 22. Two rollers 29 that are rotatable about their shafts 30 and that serve as support for the cam plate 20 are positioned at an opposite planar surface 28 of the wedge-shaped cam plate 20, so that the cam plate is movable in a vertical direction only.

The respective lengths of the lever arms or members 12 and 13 are selected such that the force that serves as the weight counterbalance for the arrangement of the arm members 7 and 8 is constant independently of the position of the arm members 7 and 8. The length of the lever member 13 of the second arm member 8 is selected such that the constant force balances out the dead weights of the arm member 8 and the x-ray tube 11 about the shaft 10. The length of the lever member 12 of the first arm member 7 is selected such that the constant force serves as a weight counterbalance for the combined dead weight of the first arm member 7, the second arm member 8, and x-ray tube 11 about the shaft 9.

The above-described, wedge-shaped cam plate 20 and the roller 21 that engages the surface 27 of the cam plate 20 under the bias of the spring 22 generates the constant force that is required in order to balance out the arrangement of arm members 7 and 8 with the x-ray tube 11. The slope along the surface 27 thereby comprises a curve such that a sub-force corresponding to the constant force arises independently of the vertical position of the cam plate 20 relative to the roller 21, arising within certain limits that are shown in FIG. 1 as an upper and as a lower limit. The potential, upper limit of the cam plate 20 relative to the roller 21 is depicted by the cam plate 20 illustrated with solid lines. The lower limit is depicted by the cam plate 20 illustrated with broken lines. The curve of the surface 27 presented to the roller 21 at the upper limit of the plate 20 is selected such that the sub-force is lower than the constant force. When the cam plate 20 is brought into this position, i.e. when the roller 21 presses against the surface 27 at the narrow part of the cam plate 20, the cam plate 20 is situated in its lowest position.

The position of the wedge-shaped cam plate 20 is dependent on the position of the arm members 7 and 8 that in turn influence the parallelogram system. In the exemplary embodiment, the parallelogram system is a parallelogram arm arrangement formed of the first arm member 7 with its lever member 12 that together form a first longitudinal brace or segment; of the lever member 13 of the second arm member 8 that forms a first cross brace or segment; the longitudinal stay 31 hingedly connected to both the free end of the lever member 1 and to the node 18 at one end of the cross stay 32 that forms a second longitudinal brace or segment; and the cross stay 32 that forms a second cross brace or segment.

When the x-ray tube 11 is moved down so that the second arm member 8 assumes the position that is illustrated by a broken line, the parallelogram arm arrangement having segments 7 & 12, 13, 31, and 32 is turned around its connecting nodes 15 through 18 into a position that is also illustrated by broken lines. As a result thereof, the connecting node 18 pulls the cam plate 20 vertically upward via the brace 19, so that the cam plate 20 assumes the lower limit position that is illustrated by broken lines.

When the x-ray tube 11 is moved in an upward direction, the cam plate 20 is moved vertically downward into a position in which the roller 21 presses against the surface 27 of the cam plate in the narrower part thereof. In this position, the cam plate 20 represents an automatic, upper end position stop for the x-ray tube 11. This position can be an ideal focus-to-film spacing into which the x-ray tube 11 can be quickly moved.

When the x-ray tube 11 is displaced in an upward direction, the cam plate 20, independently of the motions of the arm members 7 and 8 around the shafts 9 and 10, moves by a corresponding amount in the vertical direction. When the x-ray tube 11 is moved in a horizontal plane with the arm members 7 and 8, the cam plate 20 does not displace or displaces to a negligible degree, this meaning that the spring 22 is not influenced by such a motion, this in turn increasing the useful life thereof.

It can also be appreciated from FIG. 1 that the brace 19 is hingedly connected to the cam plate 20 via a shaft 33 as well as to the connecting node 18. Thus, the brace 19 can turn about the shaft 33 when the connecting node 18 is laterally displaced, i.e., when the arm members 7 and 8 or, respectively, the x-ray tube 11 are moved.

In order to compensate for the counter-rotation lateral forces to which the brace 19 is exposed when it is turned about the shaft 33, the brace 19 preferably is connected to a force compensating arrangement 34. The force compensating arrangement is illustrated in greater detail in FIG. 2.

As illustrated in FIG. 2, the force compensating arrangement 34 preferably comprises a bipartite articulated arm arrangement wherein the free end of one arm 35 is rotatably connected to the brace 19 via a shaft 37. The free end of a second arm 36 is rotatably secured via a shaft 38 to a sleeve 39 attached to the brace 19, this sleeve 39 operatively being seated so as to be displaceable along the axis of the brace 19. A common articulating axis 40 for the arms 35 and 36 is seated between two rails 41 and 42 that extend parallel to one another and that are vertically oriented and rigidly connected to the truck 2.

The second arm 36 is influenced by a compression spring 43 whose one end 44 presses against a sleeve 46 that is rigidly connected to the brace 19 and whose other end 45 is connected to the free end of the second arm 36 via the sleeve 39. As a result of the compression spring 43, the free end of the second arm 36 is influenced via the sleeve 39 by a force in the axial direction of the brace 19, in the direction onto the free end of the first arm 35.

When the brace 19 has assumed the position illustrated in FIG. 2, the brace 19 is held in place with the assistance of the force compensating arrangement 34. The lateral force that the brace 19 is subjected to in its oblique attitude is compensated for by the force compensating arrangement 34 with a force that corresponds to the lateral force.

As a consequence of the structural design of the force compensating arrangement 34, the force compensating arrangement 34 acts in the same fashion regardless of the angle that the brace 19 describes with respect to the rails 41 and 42. The rails 41 and 42 are arranged such that the brace 19 can pass through them, this being illustrated by the broken line illustration of the brace 19. As illustrated, the arms 35 and 36 turn around the common articulated axis 40 given such a motion.

Within the framework of the idea of the invention, the parallelogram system can also be formed with other structural means in addition to being formed with arms and braces.

While a preferred embodiment has been shown, modifications and changes may become apparent to those skilled in the art which shall fall within the spirit and scope of the invention. It is intended that such modifications and changes be covered by the attached claims.

We claim:

1. A weight counterbalancing means for an x-ray apparatus articulating arm having first and second arm members, one end of the first arm member being hingedly secured to the x-ray apparatus and operative to rotate about a first horizontal axis and the other end of the first arm member being hingedly connected via a second horizontal axis to one end of the second arm member at whose other end an apparatus is secured, each arm member being provided with a lever member that is part of a parallelogram system whose connecting nodes comprise in part an end of the lever arm of the first arm member not connected in the first arm member; in part the hinged connection between the first and second arm member; and in part an end of the lever arm of the second arm member not connected to the second arm member, only a remaining connecting node of the parallelogram system being directly subject to a vertically directed constant force that counterbalances the articulating arm around the first, horizontal axis so that the articulating arm is held in equilibrium in every position, the vertically directed constant force being exerted by a counterbalance that is hingedly connected to the remaining connecting nodes such that the counterbalance in every position of the arm members is directed downward, the vertically directed constant force being provided in part by a weight that is secured to the remaining connecting node, the weight secured to the remaining connecting node being a wedge shape member with at least one sloped surface and whose movement is restricted to a vertical direction, a spring providing a biasing force against the sloped surface of the wedge-shaped member such that a vertically directed sub-force that serves in part as the constant force arises, and the lever members having a length such that the force that counterbalances the articulating arm is constant independently of the position of the articulating arm.

2. The weight counterbalancing means of claim 1, wherein the slope of the sloped surface of the wedge shaped member follows a substantially vertical curve such that the sub-force is constant, between limits, independently of the vertical position of the wedge-shaped member.

3. The weight counterbalancing means of claim 2, wherein the curve is constructed such that, beyond one of the limits, the sub-force is lower than the constant force.

4. The weight counterbalancing means of claim 1, wherein the spring is a compression spring having one end secured to the x-ray apparatus and another end secured to a roller, said roller being biased against the sloped surface of the wedge-shaped member by the spring roughly in a horizontal direction.

5. The weight counterbalancing means of claim 1, wherein the wedge-shaped member is connected to the remaining connecting mode via a brace.

6. The weight counterbalancing means of claim 5, wherein the force is exerted by a compression spring whose one end is supported against the brace and whose other end is connected to the free end of the second arm.

7. A counterbalance articulating arm comprising:
a base;
a first arm member having a base end and a node end, said base end of said first arm being hingedly secured to said base;
a second arm member having a base end and a node end, said base end of said second arm member being hingedly secured to said free end of said node arm member;
a first lever member having a base end secured to said base end of said first arm member and a node end extending in a direction directly opposite said free end of said first arm member;
a second lever member having a base end secured to said base end of said second arm member and a node end extending directly opposite said free end of said second arm member; and
a parallelogram, three nodes of which comprise said node ends of said first and second lever members and said hinge connection between said first and second arm members, only a fourth node of which being directly subject to a vertically directed constant force that is constant, within limits, regardless of a position of said first and second arm members so as to equally counterbalance said first and second arm members, the vertically directed force being exerted by a counterbalance that is hingedly connected to the fourth node such that the counterbalance in every position of the arm members is directed downward, the lever members having a length such that the force that counterbalances the articulating arm is constant independently of the position of the articulating arm, the counterbalance comprising a weight secured from said fourth node, said weight having a sloped camming surface, and a camming member operatively biased against said camming surface so as to generate a vertical downward force that provides said constant force.

8. The counterbalanced articulating arm of claim 7, wherein said weight is rotatably secured to said fourth node.

9. A weight counterbalanced arm comprising:
a first arm having one end hingedly secured to a base so as to be operative to pivot about a first horizontal axis;
a second arm having one hingedly secured to another end of said first arm so as to be operative to pivot about a second horizontal axis;

a first lever member secured to and extending from said first arm and said first horizontal axis along a longitudinal axis of said first arm;

a second lever member secured to and extending from said second arm and said second horizontal axis and along a longitudinal axis of said second arm;

a longitudinal stray having one end hingedly secured to an end of said second lever member not connected to said second arm member;

a cross stray member having one end hingedly secured to an end of said first lever member not connected to said first arm member and another end hingedly connected to another end of said longitudinal stay; and a parallelogram having three nodes comprising the end of said first lever not connected to said first arm member and both ends of said second lever, and a fourth node comprising said connection between said longitudinal stray and said cross stray, said fourth node being subject to a vertically directed force that is constant, within limits, independent of a position of said counterbalanced arm, the vertically directed force being exerted by a counterbalance that is hingedly connected to the fourth node such that the counterbalance in every position of the arm members is directed downward, and the lever members having a length such that the force that counterbalances the articulating arm is constant independently of the position of the articulating arm, the counterbalance comprising a weight secured from said fourth node, said weight having a sloped camming surface, and a camming member operatively biased against said camming surface so as to generate a vertical downward force so that provides said constant force.

10. The weight counterbalanced arm of claim 9, wherein said weight is rotatably secured to said fourth node.

11. In an x-ray apparatus having an extending arm comprising a first arm with a base and hingedly attached to a base and operative to pivot about a first horizontal axis and a second arm having a base end hingedly attached to another end of said first arm and operative to pivot about a second horizontal axis, and an x-ray tube being attached to the other end of the second arm, the improvement comprising:

a lever member secured to the base end of each of said first arm and second arm, each lever arm extending along a longitudinal axis of its associated first or second arm; and a parallelogram system having three nodes comprised of said first horizontal axis, said second horizontal axis, and a end of said lever arm secured to said second arm, and having a fourth node which is connected to a vertically directed force operative to compensate to the weight of said first arm and said second arm about said first horizontal axis so that said first arm and said second arm are operatively held, within limits, in equilibrium in every position, the vertically directed force being exerted by a counterbalance that is hingedly connected to the fourth node such that the counterbalance in every position of the arm member is directed downward, and the lever members having a length such that the force that counterbalances the articulating arm is constant independently of the position of the articulating arm, the counterbalance force securing a weight secured from said fourth node, said weight having a sloped camming surface, and a camming member operatively biased against said camming surface so as to generate a vertical downward force that serves as said constant force.

12. The counterbalancing articulating arm of claim 11, wherein said weight is rotatably secured to said fourth node.

* * * * *